US00PP36366P2

(12) United States Plant Patent
Heuger

(10) Patent No.: US PP36,366 P2
(45) Date of Patent: Dec. 31, 2024

(54) ***HELLEBORUS* PLANT NAMED 'HM 1220'**

(50) Latin Name: ***Helleborus ballardiae* X *Helleborus* x *hybridus***
Varietal Denomination: HM 1220

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,435

(22) Filed: Nov. 14, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

(56) References Cited

PUBLICATIONS

Zakreti 2023 Hellebore (*Helleborus x iburgensis*) 'HGC ice N' roses' retrieved on Apr. 16, 2024 at https://zielonozakreceni.pl/forum/ciemierniki/11877-ciemiernik-iburgski-helleborus-x-iburgensis-hgc-ice-n-roses-macy-marble-hm-1212#286241.*

* cited by examiner

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Helleborus* plant named 'HM 1220', characterized by its upright to somewhat outwardly spreading and mounded plant habit; moderately vigorous to vigorous growth habit; dark green-colored leaflets with lighter green-colored venation; freely flowering habit; light pink and purplish red-colored flowers; and good garden performance.

1 Drawing Sheet

Figure 1:
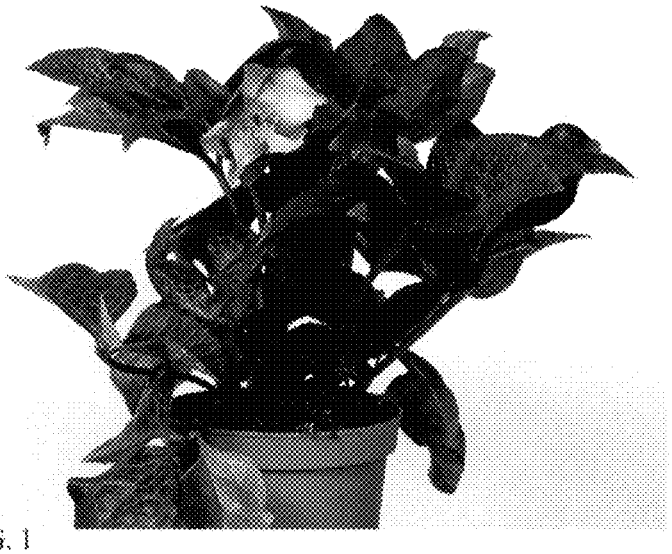

Botanical designation: *Helleborus ballardiae* X *Helleborus* x *hybridus.*

Cultivar denomination: 'HM 1220'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1378. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ballardiae* X *Helleborus* x *hybridus* and hereinafter referred to by the name 'HM 1220'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in January 2015 of a proprietary selection of *Helleborus ballardiae* identified as code number P482, not patented, as the female, or seed, parent and a proprietary selection of *Helleborus* x *hybridus* identified as code number O1652, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2017.

Asexual reproduction of the new *Helleborus* plant by in vitro axillary meristem culture in a controlled environment in Glandorf, Germany since May, 2017 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HM 1220'. These characteristics in combination distinguish 'HM 1220' as a new and distinct *Helleborus* plant:

1. Upright to somewhat outwardly spreading and mounded plant habit.
2. Moderately vigorous growth habit.
3. Dark green-colored leaflets with lighter green-colored venation.

4. Freely flowering habit.
5. Light pink and purplish red-colored flowers.
6. Good garden performance.

Plants of the new *Helleborus* differ from plants of the female parent selection in the following characteristics:

1. Leaf venation of leaflets of plants of the new *Helleborus* is more distinct than leaf venation of leaflets of plants of the female parent selection.
2. Flowers of plants of the new *Helleborus* are light pink and purplish red in color whereas flowers of plants of the female parent selection are creamy white to pink in color.

Plants of the new *Helleborus* differ from plants of the male parent selection in the following characteristics:

1. Leaf venation of leaflets of plants of the new *Helleborus* is more distinct than leaf venation of leaflets of plants of the male parent selection.
2. Flowers of plants of the new *Helleborus* are light pink to purplish red in color whereas flowers of plants of the male parent selection are pink in color.

Plants of the new *Helleborus* can also be compared to plants of *Helleborus* x *ericsmithii* X *Helleborus* x *hybridus* 'COSEH 4500', disclosed in U.S. Plant Pat. No. 28,293. In side-by-side comparisons, plants of the new *Helleborus* differ primarily from plants of 'COSEH 4500' in the following characteristics:

1. Leaf venation of leaflets of plants of the new *Helleborus* is more distinct than leaf venation of leaflets of plants of 'COSEH 4500'.
2. Flowers of plants of the new *Helleborus* are light pink and purplish red in color whereas flowers of plants of 'COSEH 4500' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant. The photograph at the top of the sheet (FIG. 1) is a side perspective view of a typical flowering plant of 'HM 1220' grown in a container.

Figure 2:
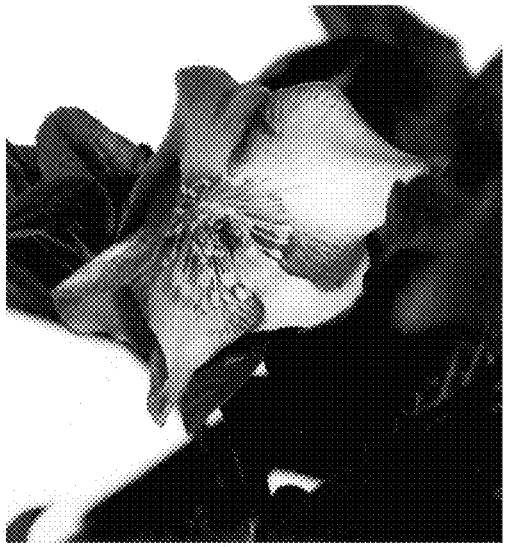

The photograph at the bottom of the sheet (FIG. 2) is a close-up view of a typical flowering plant of 'HM 1220'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ballardiae* X *Helleborus* x *hybridus* 'HM 1220'.

Parentage:

*Female, or seed, parent*.—Proprietary selection of *Helleborus ballardiae* identified as code number P482, not patented.

*Male, or pollen, parent*.—Proprietary selection of *Helleborus* x *hybridus* identified as code number O1652, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within the foliar plane; plant shape, roughly globular; moderately vigorous growth habit and moderate growth rate.

*Plant height, soil level to top of foliar plane*.—About 25.8 cm.

*Plant height, soil level to top of flowers*.—About 24 cm.

*Plant diameter* (*area of spread*).—About 45.9 cm.

Leaf description:

*Arrangement*.—Leaves arranged in a basal rosette; leaves palmately compound with typically five, or occasionally three, leaflets per leaf.

*Leaf length*.—About 20.8 cm.

*Leaf width*.—About 23.5 cm.

*Leaflet length*.—About 14 cm.

*Leaflet width*.—About 7.2 cm.

*Leaf shape*.—Palmate; roughly reniform in outline.

*Leaflet shape*.—Elliptic to ovate, occasionally obovate.

*Leaflet apex*.—Bluntly acute.

*Leaflet base*.—Attenuate.

*Leaflet margin*.—Serrate; moderately coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; moderately glossy to glossy.

*Leaflet venation pattern*.—Pinnate and reticulate.

*Leaflet color*.—Developing leaflets, upper surface: Close to a blend of NN137A and 147A; towards the base, tinged with close to 183A to 183B; venation, close to 146B. Developing leaflets, lower surface: Close to 148A strongly tinged with close to N200A; venation, close to 183A. Fully developed leaflets, upper surface: Close to than 139A; towards the base, tinged with close to a blend of N186C and 200A; venation, close to 144A. Fully developed leaflets, lower surface: Close to a blend of 147B and 148A; venation, close to 183A.

*Petioles*.—Length: About 17.3 cm. Diameter: About 5 mm by 6 mm. Strength: Strong. Texture and luster, upper and lower surfaces: Smooth, glabrous; moderately glossy. Color, upper surface: Close to 146B; moderately to heavily covered with fine dots, close to N186C. Color, lower surface: Close to 146B; proximally, close to 187A; moderately to heavily covered with fine dots, close to N186C.

Flower description:

*Flower shape and habit*.—Single rotate bowl-shaped flowers arranged in panicles; freely flowering habit with about nine flowers per inflorescence and about 18 flowers and flower buds per plant; flowers face mostly outwardly to slightly nodding.

*Fragrance*.—None detected.

*Natural flowering season*.—Plants begin flowering about ten months after planting; plants flower naturally from late autumn into the winter in Germany.

*Flower longevity on the plant*.—About ten days; sepals persistent, other flower parts are not persistent.

*Flower buds*.—Length: About 2.2 cm. Diameter: About 1.2 cm. Shape: Elliptic to oblong. Texture and luster: Smooth, glabrous; matte. Color: Close to 150D; towards the apex, tinged with close to 182A and 182B.

*Inflorescence height* (*including peduncle*).—About 26 cm.

*Inflorescence diameter*.—About 18.5 cm.

*Flower diameter*.—About 8.6 cm.

*Flower depth*.—About 3.4 cm.

*Petals*.—All petals are transformed into nectaries.

*Sepals*.—Quantity and arrangement: About five, arranged in a single whorl. Length: About 5 cm. Width: About 4.8 cm. Shape: Broadly ovate to close to rhomboidal; slightly concave. Apex: Rounded. Base: Cuneate. Margin: Entire; coarsely undulate. Texture and luster, upper surface: Smooth, glabrous; matte. Texture and luster, lower surface: Smooth, glabrous; slightly glossy. Color: When opening, upper surface: Close to 150D; center, close to 157A; towards the margins, tinged with close to N186D. When opening, lower surface: Close to 145D; towards the margins and apex, strongly tinged with close to N186D. Fully opened, upper surface: Close to a blend of 49D and N155C strongly tinged with close to N77B; towards the apex, strongly tinged with close to 145B; venation, similar to lamina colors; with subsequent development, color becoming closer to 146D with margins, close to 70A. Fully opened, lower surface: Close to 145A and 145B; towards the apex, base and margins, strongly tinged with close to 187B and 187C; venation, similar to lamina colors; with subsequent development, color becoming closer to 183C tinged with close to 146D.

*Flower bracts*.—Quantity per flower: Typically one. Length: About 11.1 cm. Width: About 6.7 cm. Shape: Ovate to broadly obovate. Apex: Acute to three-parted. Base: Truncate to cuneate. Margin: Serrate; coarsely undulate. Color, upper surface: Close to a blend of NN137A and 147A; venation, close to 144A and midvein, tinged with close to 187A. Color, lower surface: Close to 148A strongly tinged with close to 200B; midvein, close to 187B.

*Peduncles*.—Length: About 19 cm. Diameter: About 6.5 mm to 7 mm. Aspect: About 20 degrees from vertical. Strength: Strong. Texture and luster: Smooth, glabrous; moderately glossy. Color: Close to 146C to 146D; moderately to heavily covered with fine dots, close to 184A.

*Pedicels*.—Length: About 4.6 cm. Diameter: About 3.5 mm. Aspect: About 45 degrees from peduncle axis. Strength: Moderately strong. Texture and luster: Sparsely pubescent; slightly glossy. Color: Close to 146D to lighter than 146D; heavily covered with fine dots, close to 181A and 181B.

*Reproductive organs*.—Stamens: Quantity per flower: About 75. Filament length: About 1.7 cm. Filament color: Close to 150C to 150D. Anther shape: Double and broadly reniform; basifixed. Anther size: About 2.5 mm by 3.5 mm. Anther color: Close to 154C to 154D. Pollen amount: Sparse. Pollen color: Close to 4D to lighter than 4D. Pistils: Quantity per flower: About four. Pistil length: About 1.2 cm. Stigma diameter: About 0.3 mm. Stigma shape: Club-shaped. Stigma color: Close to 150D. Style length: About 1.15 cm. Style color: Close to 186A. Ovary color: Close to 150D. Nectaries (transformed petals): Quantity per flower: About 13. Length: About 9 mm. Diameter: About 4 mm. Shape: Tubular, flattened; apices, obtuse. Texture and luster, inner and outer surfaces: Smooth, glabrous; slightly glossy. Color, immature, inner and outer surfaces: Close to 144C; towards the base, close to 146C. Color, mature, inner and outer surfaces: Close to 144C; towards the apex, close to 151B; towards the base, close to 146C; venation, similar to lamina colors; with subsequent development, close to N144A, towards the apex, close to 153C and towards the base, close to 146C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HM 1220' as herein illustrated and described.

* * * * *